United States Patent [19]
Carlson

[11] 4,085,782
[45] Apr. 25, 1978

[54] VACCINE AND MEDICAMENT DISPENSING SYSTEM

[76] Inventor: Harold W. Carlson, 18070 Wildemere, Detroit, Mich. 48221

[21] Appl. No.: 689,008

[22] Filed: May 24, 1976

[51] Int. Cl.² .............................................. B65B 3/04
[52] U.S. Cl. ...................................... 141/1; 222/129; 222/400.7
[58] Field of Search ................................. 141/1, 2, 18; 222/400.7, 129, 66; 128/214 R, 214 F, DIG. 12

[56] References Cited

U.S. PATENT DOCUMENTS

| | | | |
|---|---|---|---|
| 2,202,163 | 5/1940 | Nulford et al. | 128/214 R |
| 2,693,801 | 11/1954 | Foreman | 128/214 F |
| 2,794,437 | 6/1957 | Tash | 128/214 F |
| 3,128,917 | 4/1964 | Krause | 128/214 R |
| 3,527,391 | 9/1970 | Muria | 222/400.7 |

Primary Examiner—Houston S. Bell
Attorney, Agent, or Firm—Harness, Dickey & Pierce

[57] ABSTRACT

A multiplicity of vials containing the same vaccine or medicament are connected together in series and a pressure source is connected to the first vial to apply above ambient pressure to it and to the remaining vials, the last vial in the series being used by medical personnel to fill syringes.

4 Claims, 2 Drawing Figures

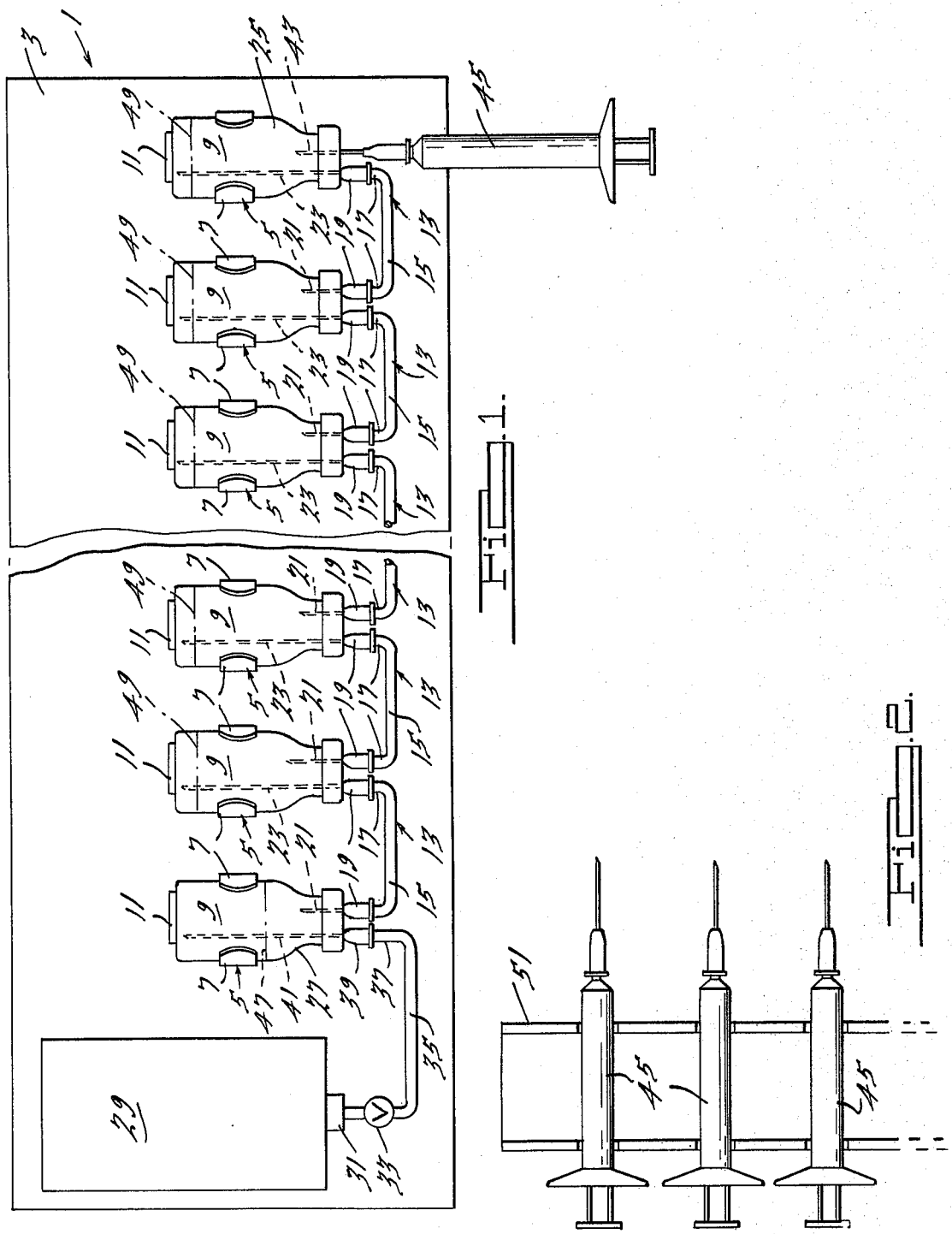

VACCINE AND MEDICAMENT DISPENSING SYSTEM

BACKGROUND OF THE INVENTION

In the various healing professions dealing with all phases of care of humans and animals it is customary to furnish vaccines or medicaments in relatively small vials having a permanent cap of resilient material that can be penetrated by the needle of a syringe but which seals itself upon withdrawal of the needle to maintain the vial in fluid tight condition. These vials are relatively small in size and hold only enough material for a small number of injections. In cases where a large number of people (or animals) are to be injected, the ordinary syringe filling procedure is relatively slow and inefficient because it takes longer to fill the syringe, especially when the vial is almost empty, than it does to give the injection and several trained people are required merely to fill the syringes require for use by one doctor who is giving the injections.

BRIEF SUMMARY OF THE INVENTION

It is the purpose of this invention to increase the speed and efficiency of the medical syring filling procedure.

The invention accomplishes this purpose by connecting a number of medical vials in series so that the contents of one vial can flow into the next. Preferably, above ambient pressure is applied to the liquid in the first vial in the series to force liquid to flow toward the last vial. Syringes are, of course, filled by insertion into one of the downstream vials, preferably the last. With this arrangement, the upstream vials will empty first and can be replaced without interrupting the use of the downstream vials which are maintained in a continuously filled condition.

DESCRIPTION OF THE DRAWINGS

FIG. 1 is a front view of a panel for supporting a series of vials in accordance with the invention; and FIG. 2 is a rack holding a number of syringes after filling by means of the invention.

DESCRIPTION OF THE INVENTION

The vaccine and medicament dispensing system 1 includes a rectangular support board 3 that may be readily mounted on a wall, table, etc. in a hospital, clinic, medical or veterinary office, etc. It has a series of vial clamps 5 secured to its face as by screws, rivets, etc. (not shown). The clamps have resilient side arms 7 which can be spread apart to insert or remove the vials 9 and top flanges 11 which engage the ends of the vials to position them and permit needles to be inserted into and through the usual flexible, seal sealing membranes (not shown) at the narrow ends of the bottles. The vials 9 are lined up in series and any number can be used; it being presently contemplated that for rapid mass inoculations perhaps 15 or 20 vials would be mounted on the board 3.

The vials are connected in series relationship by a plurality of tubular conduit members 13 which may be of substantially identical construction though reversed from one to another. The members 13 each include a horizontal conduit portion 15 which is upturned at each end as shown at 17, the upturned ends being inserted in a fitting or coupling 19 that carries a short hollow needle 21 at one end and a long hollow needle 23 at the other end. These can be substantially the same as those used on syringes. The short needle 21 is an outlet for the vial in which it is inserted and is just long enough to maintain whatever minimum level of liquid is desired. The long needle is the inlet for the vial in which it is inserted and is long enough to reach close to the top end of a vial 9 in its inverted position on the board 3. It can be readily seen from FIG. 1 how the tubular connector members 13 enable liquid to flow from one vial to the next, moving from left to right. In order to insure flow, rather than rely on vacuum induced by removal of liquid from the last vial 25, it is preferred to connect a pressure source to the first vial 27 in the series and a pressure storage vessel 29 containing sterilized air under pressure is shown as mounted on the upstream end of the board 3. Its outlet 31 delivers air to a control valve 33 including, if required, pressure reducing means which in turn delivers air to an inlet conduit 35 for the system 1. The outlet end 37 of conduit 35 has a coupling or fitting 39 carrying a long hollow needle 41 which may, respectively, be substantially identical to the couplings 19 and long needles 23. The control valve 33 is set so that the pressure is very low, just high enough to force flow from vial 27 toward vial 25. It is contemplated that 2-5 psi will be sufficient pressure.

In use, the nurse, doctor, or technical assistant can insert the needle 43 of a syringe 45 into the last vial 25 and withdraw the desired amount of liquid. This will be reflected by a reduction in volume of fluid in vial 25. However, the air pressure at the top of the first vial 27 will force the liquid to flow through the system to replace that which was withdrawn from vial 25, this being illustrated by the lowered level 47 of liquid in vial 27. The levels 49 in the remaining vials will probably remain approximately the same, After enough syringes have been filled to the desired degree with liquid from the vial 25 to empty vial 27, then the vial next to vial 27 will gradually lose liquid and so on. At some time prior to the last vial 25 losing its level, the air pressure can be turned off by valve 33 and the depleted upstream vials 9 can be replaced with full vials. While the emptied vials are being replaced, filling of syringes from vial 25 can continue.

The syringes can be filled as rapidly as needed and they can be stored in filled condition in a suitable rack 51 from which they can be easily handed to the person making the injection into living tissue.

Modifications can be made in the specific structures illustrated. For example, if the pressure source 29 is itself at a very low pressure which can be directly applied to the system, e.g. 2-5 psi, the valve 33 will be unnecessary and by making the conduit 35 of resilient, flexible tubing material pressure can be cutoff by simply applying a common tube clamp (not shown) to the tubing. Similarly, all of the conduits could, and preferably are, made of flexible tubing to facilitate assembly and enable the use of clamps at any point in the system to cutoff flow and isolate one or more parts of the system.

I claim:

1. In a dispensing system for liquid vaccine and medicaments contained in conventional vials for supplying liquid to syringes inserted into the vials, a support board, a series of vial clamps supported on said board, a series of vials containing said liquid in said clamps and disposed so that the vials are upside down with the liquid resting on the penetratable self sealing membrane in the vial, there being a first vial in said series and a last vial in said series and a multiplicity of vials in said series between said first and last, conduits operatively interconnecting said vials for the continuous flow of liquid from one vial to the adjacent vial and the direction of flow being from the first vial toward the last vial, and a source of low fluid pressure operatively connected to said first vial to apply a low fluid pressure to said liquid in all said vials and pressurize flow toward the last vial whereby the last vial is continuously supplied with liquid from the remaining vials.

2. A system as set forth in claim 1 wherein substantially each of said conduits has a relatively short hollow syringe-type needle at one end inserted into a vial to form an inlet for liquid to flow from the vial into the conduit and a relatively long hollow syringe-type needle at the other end inserted into the adjacent vial to form an outlet for liquid to flow from the conduit into the adjacent vial.

3. The method of increasing the efficiency with which syringes are filled with liquid vaccine or medicament which comprises arranging a multiplicity of conventional vials containing said liquid so that the vials are upside down with the liquid resting on the penetratable self sealing membrane in the vial, inserting syringe-type needles through the membrane, attaching tubing to said needles and interconnecting said vials in series relationship so that liquid flows in series from one vial to the adjacent vial in a direction from the first to the last of the vials in the series, supplying a fluid at a pressure slightly above ambient to the first in said series of vials to thereby pressurize the liquid in the vial-conduit system, and withdrawing liquid from the last of the vials by insertion of a syringe into the last of said vials to fill said syringe with a desired amount of said liquid.

4. A method as set forth in claim 3 including a final step of placing the syringes as they are filled on a storage rack for subsequent use to inject said liquid into living tissue.

* * * * *